United States Patent [19]

Sabarino et al.

[11] Patent Number: 5,714,623
[45] Date of Patent: Feb. 3, 1998

[54] PROCESS FOR THE PREPARATION OF CARBOXYLIC ACIDS AND ESTERS THEREOF BY OXIDATIVE CLEAVAGE OF UNSATURATED FATTY ACIDS AND ESTERS THEREOF

[75] Inventors: Giampiero Sabarino, Vercelli; Andrea Gardano, Trino; Marco Foa', Novara, all of Italy

[73] Assignee: Novaol S.r.l., Ravenna, Italy

[21] Appl. No.: 433,393

[22] PCT Filed: Oct. 25, 1993

[86] PCT No.: PCT/EP93/02944

§ 371 Date: May 1, 1995

§ 102(e) Date: May 1, 1995

[87] PCT Pub. No.: WO94/10122

PCT Pub. Date: May 11, 1994

[51] Int. Cl.[6] .................... C07C 51/16; C07C 51/235
[52] U.S. Cl. .................... 554/132; 554/156; 252/367; 252/368; 252/369; 562/523; 562/538; 562/539
[58] Field of Search .................... 554/134, 135, 554/136, 132, 156; 252/367, 368, 369

[56] References Cited

U.S. PATENT DOCUMENTS

| | | | |
|---|---|---|---|
| 3,895,040 | 7/1975 | Miyazaki et al. | 260/413 |
| 4,550,196 | 10/1985 | Venturello et al. | 562/418 |
| 4,606,863 | 8/1986 | Nakazawa et al. | 260/413 |

*Primary Examiner*—Gary Geist
*Assistant Examiner*—Deborah D. Carr
*Attorney, Agent, or Firm*—Bryan Cave LLP

[57] ABSTRACT

A process for the preparation of carboxylic acids and esters thereof, which involves the steps of (a) mixing an unsaturated fatty acid or corresponding ester with an oxidative substance in the presence of a catalyst selected from the group consisting of oxides of tungsten and molybdenum and their acids and alkaline salts, (b) reacting the product mixture from step (a), which comprises vicinal diols, with oxygen or an oxygen-containing gas in the presence of a cobalt-containing compound which acts as a catalyst. The product mixture from step (a) is not subjected to any purification treatments prior to undergoing step (b).

8 Claims, No Drawings

PROCESS FOR THE PREPARATION OF CARBOXYLIC ACIDS AND ESTERS THEREOF BY OXIDATIVE CLEAVAGE OF UNSATURATED FATTY ACIDS AND ESTERS THEREOF

This application is a 371 of PCT/EP93/02944 filed Oct. 25, 1993.

FIELD OF THE INVENTION

The present invention relates to a process for the production of carboxylic acids and esters thereof comprising the operation of:

Reacting an unsaturated fatty acid or corresponding ester with an oxidising compound, in the presence of a catalyst belonging to the group consisting oxides of molybdenum and tungsten and their corresponding acids and alkaline salts, obtaining an intermediate reaction product and reacting said intermediate product with oxygen or an oxygen containing gas in the presence of a cobalt compound which acts as a catalyst.

A process of the above mentioned type, that is defined on the whole as an oxidative cleavage, is described in the following consecutive reaction I and II, where the intermediate product is a vicinal diol in which the hydroxy groups are attached to the carbon atoms that in the starting compound were connected with a olefinic double bond:

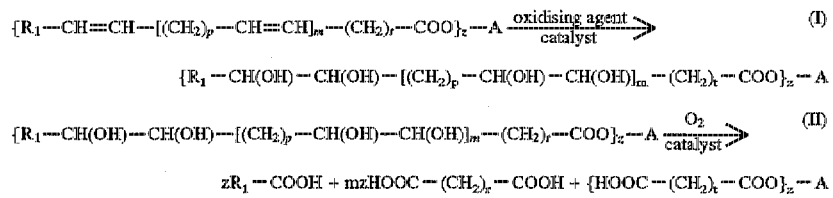

where $p=0-1$, $m=0-2$, $t=0-11$, $z=1-3$;

$R_1$=H, $C_1$–$C_8$ alkyl or a $CH_3$—$(CH_2)_3$—$CH(OH)$—$CH_2$ radical and in which if $z=1$, A is H or $C_1$–$C_5$;

if $z=2-3$, A is the residue of a bivalent or trivalent alcohol.

DESCRIPTION OF THE PRIOR ART

The U.S. Pat. No. 4,606,863 describes a process of the above indicated type in which in certain embodiments the starting fatty acid/ester is oxidised with hydrogen in the presence of a catalyst based on tungsten or molybdenum and a solvent such as acetic acid.

The intermediate reaction product so obtained, which may contain vicinal diols or epoxy groups, ethers or esters, are purified from the solvent and water formed in the course of the reaction. They are then subjected to further oxidation with oxygen or an oxygen containing gas in the presence of a heavy metal compound, for example cobalt, and a bromine or chlorine compound.

In addition, if the intermediate product has a high melting point or if it is necessary to get rid of a notable heat of reaction, a polar organic solvent, such as $C_2$–$C_{10}$ saturated carboxylic acid, is used as the reaction solvent.

The process described by U.S. Pat. No. 4,696,863 has the inconvenience of requiring a purification treatment of the intermediate reaction products and the additional presence of a bromine or chlorine compound, in order to activate the heavy metal acting as a catalyst, and optionally an organic solvent. The process as a whole moreover lacks selectivity with respect to the formation of specific compounds.

U.S. Pat. No. 3,711,523, U.S. Pat. No. 3,816,525 and British Patent 1,405,578 describe oxidation processes of vicinal diols or epoxides in order to obtain carboxylic acids with an oxidising system consisting of peroxides such as peracetic acid, and oxygen or an oxygen containing gas in the presence of a cobalt based catalyst.

Such processes are not adapt for industrial scale production as they use dangerous and costly reagents such as peracetic acid. Moreover, they are preferably carried out in organic solvents with the additional complication arising from the separation of the reaction products there from, which in itself creates an additional cost.

British Patent 1,330,205 describes a process for the production of carboxylic acids through oxidation of vicinal diols using a catalyst system comprising a cobalt salt such as acetate in the presence of a pertungsten or permolybdenum acid or similar compounds in a bipolar aprotic solvent.

Such a process has the disadvantage of requiring the use of costly and difficultly recyclable solvents and requires that the diols to be oxidised are anhydrous.

It is in fact known that water has an adverse effect on the bipolar aprotic solvents in that it eliminates a positive effect that said solvents have in the oxidative cleavage reaction (see Tetrahedron Letters 54, pag. 5689, 1968, Pergamon Press). The reason for such an effect is probably due to the fact that the catalytic action of the cobalt salt appears to be connected to the formation of a super red Co(III) complex (see R. A. Sheldon, and J. K. Kochi in "Metal-Catalysed Oxidations of Organic Compounds", 1981, Academic Press, Pages 75 and 144) and the formation of Co(III) compound is highly disactivated by the presence of water (see F. A. Cotton and G. Wilkinson in "Advanced Inorganic Chemistry", Editor John Wiley & Sons, page 768).

U.S. Pat. No. 3,865,856 describes a process for the production of carboxylic acids by oxidation of vicinal diols with oxygen or an oxygen containing gas in the presence of a transition metal, which acts as a catalyst, and a solvent such as a hydrocarbon or saturated carboxylic acid containing at least 5 carbon atoms. According to U.S. Pat. No. 3,865,856, such solvents are necessary in order to retain aldehydes which constitute intermediate reaction products. The oxidative gas flow is moreover used to continuously eliminate water formed during the reaction.

Also said process has the inconvenience of requiring the presence of an organic solvent.

SUMMARY OF THE INVENTION

With the aim of overcoming these inconveniences, the subject of the present invention consists of a process of the above mentioned type, characterised by the fact that water, the cobalt containing compound and the oxygen or oxygen containing gas is directly added to the said intermediate reaction product, without previously having undergone any purification treatments.

The process according to the present invention has the advantage of not requiring any purification of the intermediate reaction product, essentially consisting of vicinal diols, nor does it require the presence of organic solvents in order to carry out further oxidation of the vicinal diols, which is carried out with a more than sufficient yield in the presence of water.

Such a result is completely unpredictable and surprising considering the numerous prior art documents mentioned above relating the opposite effect, which would be the effect of water on the catalytic properties of cobalt, and also the scarce solubility of oxygen in water with respect to other organic solvents (see the table reported on page 320 of "Chemistry and Industry" no. 22, 1985).

DETAILED DESCRIPTION OF THE INVENTION

On the whole, the oxidative cleavage process according to the present invention uses a cobalt based catalyst, easily found in the market, a gaseous oxidant such as pure oxygen or air and water, resulting in an economical, non polluting and simple to carry out process, whilst at the same time allowing high yields and selectivity to be obtained.

The cobalt compounds which are particularly adapt as catalysts for the oxidation reaction (II) of the diols are cobalt acetate, cobalt chloride and cobalt sulphate, used in quantities between 0.1 and 3% by mole with respect to the diol.

Water is preferably added to the diols obtained by reaction (I) in order to have a weight ratio of water/diol between 1:1 and 5:1.

The oxidising substance used in carrying out reaction (I) is preferably an aqueous solution of hydrogen peroxide in concentrations comprised between 50 and 70% and used in a quantity comprised between 100 and 140% of the stoichiometric quantity with reference to the starting materials, which corresponds to one mole of oxidising substance to one mole of double bonds to be oxidised.

The catalyst in reaction (I) is preferably present in a quantities comprised between 0.1 and 1.1% by weight with respect to the unsaturated fatty acid or ester starting materials.

The preferred reaction temperature is comprised between 50° and 90° C.

Preferably the time necessary in order to carry out the reaction (I) is comprised between 2 and 8 hours, while the time necessary to carry out reaction (II) is comprised between 5 and 12 hours.

Examples of compounds to undergo the process of oxidative cleavage are the most common fatty acids such as oleic acid, erucic acid, palmitoleic acid, myristoleic acid, 9-decalenic acid, 9-dodecalenic acid, ricinoleic acid, linoleic acid, linolenic acid, or corresponding esters with mono and polyvalent alcohols and mixtures thereof.

The process according to the present invention can be conducted by firstly carrying out reaction (I), and then charging the reactor with the diol or mixtures of diol products from reaction (I), water and the cobalt based catalyst all at once in the desired proportions. The mixture is then heated to a fixed temperature and stirred in a flow of oxygen or in the presence of air.

The reaction process is determined by controlling, from time to time, the composition of the reaction mixture by the appropriate analytical methods such as for example gas phase chromatography.

At the end of the reaction, stirring is stopped and the organic phase is separated from the aqueous phase which contains the cobalt based catalyst that can be recycled.

The reaction products can be separated using conventional techniques. The saturated mono or dicarboxylic acid esters can be, in particular, separated by fractional distillation under vacuum, while the saturated carboxylic acids can be obtained by hydrolysis of the corresponding esters or directly from the reaction mixture, exploiting the different water solubilities and boiling points.

Other advantages and characteristics of the process according to the present invention will be exemplified in the following examples, which in themselves are not intended to limit the scope of the present invention.

EXAMPLE 1

Into a round bottomed flask equipped with a mechanical stirrer, thermometer, dropping funnel and a condenser, 80 g of crude oleic acid (80% purity) containing 9% linoleic acid and 0.56 g of $H_2WO_4$ are added. The stirred mixture is brought to 60°–65° C. and 24 g of 60% w/w $H_2O_2$ is added. The addition of $H_2O_2$ is gradual over about 30 mins in order to maintain the temperature between 65°–75° C. Once the addition of $H_2O_2$ is completed the mixture is left for 1.5 hours at said temperature.

The crude reaction product so obtained is charged into a stirred 1000 ml autoclave containing 300 ml of water and 1.2 g of hydrous cobalt acetate.

The autoclave is then pressurised with 70 atm of air and the temperature is raised to 66° C. The reaction mixture is stirred at said temperature for 4.5 hours, then cooled to 50° C. and the aqueous layer is separated form the organic layer. The aqueous phase that contains the cobalt salt can be reused for the successive tests.

The organic phase is extracted another time with water at 90° C. in order to separate azelaic acid. Once cooled 30.5 g of azelaic acid is obtained. The organic phase is then fractionally distilled under vacuum (10 mm Hg) giving 25 g of pelargonic acid. The distillation residue is then saponified with aqueous NaOH at 90° C. for 1 hour. After acidification 5.5 g of azelaic acid and 2 g of pelargonic acid are separated in the above described way. The total yield is 75% of azelaic acid and 75.4% for pelargonic acid, which is reduced to about 15% carrying out a test under analogous conditions to example 1 without the presence of cobalt acetate as catalyst.

EXAMPLE 2

The same conditions as used for example 1 are used with the exception that 0.5 g of cobalt acetate is used instead of 1.2 g in the oxidation phase of the diol mixture. Proceeding as described in example 1 a yield of 70.2% of azelaic acid and 71% of pelargonic acid is obtained.

EXAMPLE 3

Into a 500 ml round bottomed flask equipped with a mechanical stirrer, thermometer, dropping funnel, gas influx tube and a condenser, 100 g of crude oleic acid (80% purity) containing 9% linoleic acid and 0.75 g of $H_2WO_4$ is added. The stirred mixture is brought to 60°–65° C. and 28 g of 60% w/w $H_2O_2$ is added. The $H_2O_2$ is gradually added over about 30 mins in order to maintain the temperature between 65°–75° C. Once the addition of $H_2O_2$ is completed the mixture is left at that temperature for 1.5 hours. Then, 200 ml of water and 1 g of hydrous cobalt acetate is added to the mixture. The temperature is raised to 70° C. by passing an oxygen stream through the reactor bottom for 4 hours. At the end of the reaction, the reaction products are recovered by the process as described in example 1, obtaining 42.5 g of azelaic acid (yield=70.9%) and 31.3 g of pelargonic acid (yield=70%).

EXAMPLE 4

Using the same apparatus as in Example 1, 100 g of crude oleic acid (80% purity) containing 9% linoleic acid and 0.75 g of $H_2WO_4$ is added. The stirred mixture is brought to 60°–65° C. and 28 g of 60% w/w $H_2O_2$ is added. The $H_2O_2$ is gradually added over about 30 mins in order to maintain the temperature between 65°–75° C. Once the addition of $H_2O_2$ is completed the mixture is left at that temperature for 1.5 hours. The crude reaction product so obtained is charged into an stirred 500 ml autoclave containing 150 ml of water and 1.0 g of hydrous cobalt chloride. The autoclave is then pressurised with 65 atm of air and the temperature is raised to 70° C. The reaction mixture is treated according to the way described in example 1 obtaining 42 g of azelaic acid (yield=70%) and 30.9 g of pelargonic acid (yield=69%).

EXAMPLE 5

Into the same apparatus of example 1, 100 g of erucic acid (95% purity) and 0.75 g of $H_2WO_4$ is added. The stirred mixture is brought to 60°–65° C. and 23.3 g of 60% w/w $H_2O_2$ is added. The $H_2O_2$ is gradually added over about 45 mins. The temperature is raised to 85° C. in order to keep the reaction mixture fluid. Once the addition of $H_2O_2$ is completed the mixture is left at that temperature for 3 hours. The crude reaction product so obtained is charged into an stirred 500 ml autoclave containing 200 ml of water and 1.0 g of hydrous cobalt acetate. The autoclave is then pressurised to 75 atm. of air and the temperature is raised to 85°–90° C. The reaction mixture is stirred at this temperature for 7 hours. At the end the reaction mixture is then cooled and extracted with ethyl ether. The ether is evaporate and the residue extracted at ambient temperature with heptane in order to separate brassilic acid from pelargonic acid. In fact a phase insoluble in heptane is obtained which is filtered and washed in heptane. The 51 g of solid phase obtained contained 43 g of brassilic acid and 4 g of pelargonic acid. From this phase practically pure brassilic acid can be obtained by crystallisation with ethanol and water.

The heptane extracts are reunited and evaporated. The residue is distilled under vacuum recovering 22.7 g of pelargonic acid.

The distillation residue is treated as indicated in example 1 obtaining 2.3 g of pelargonic acid and 3.6 g of brassilic acid.

The total yield of pelargonic acid is 64.9% and that of brassilic acid 68%.

EXAMPLE 6

Into the same apparatus as in Example 1, 100 g of crude methyl oleate (82% purity) containing 9.9% methyl linoleate, 0.75 g of $H_2WO_4$ and 1.25 g of dihydroxystearic acid is added. The stirred mixture is brought to 60°–65° C. and 28.6 g of 60% w/w $H_2O_2$ is added. The $H_2O_2$ is gradually added over about 30 mins in order to maintain the temperature between 60°–70° C. Once the addition of $H_2O_2$ is completed the mixture is left at that temperature for another 4 hours. The crude reaction product so obtained is charged into a stirred 500 ml autoclave containing 150 ml of water and 1.0 g of hydrous cobalt chloride. The autoclave is then pressurised with 75 atm of air and the temperature is raised to 65° C. The reaction mixture is stirred at this temperature for 7 hours. At the end, NaOH is added to the reaction mixture until an alkaline pH is reached and saponified for 2 hours at 95° C. After acidification with sulphuric acid, the crude reaction products are treated in the same way as described in example 1. 40.8 g of azelaic acid (yield= 70%) and 33.5 g of pelargonic acid (yield=68.8%) are obtained.

We claim:

1. A process for the preparation of carboxylic acids or esters thereof comprising the following steps:
   (a) reacting an unsaturated fatty acid or corresponding ester with an oxidizing substance in the presence of a catalyst selected from the group consisting of oxides of molybdenum, oxides of tungsten, and corresponding acids and alkaline salts of oxides of molybdenum and oxides of tungsten, to obtain an intermediate reaction product in an intermediate reaction product mixture;
   (b) reacting the intermediate reaction product with oxygen or an oxygen-containing gas in the presence of water, and a cobalt-containing compound which acts as a catalyst;
   wherein the intermediate reaction product mixture is not subjected to purification treatments prior to the addition of the cobalt-containing compound, the water, and the oxygen or oxygen-containing gas; and
   wherein the water is added to the intermediate reaction product mixture in a quantity such that the weight ratio water:intermediate reaction product is from 1:1 to 5:1.

2. The process of claim 1, wherein the cobalt-containing compound is selected from the group consisting of cobalt acetate, cobalt chloride, and cobalt sulphate.

3. The process of claim 1, wherein the cobalt-containing compound is present in an amount from 0.1 to 3% by weight with respect to the intermediate reaction product.

4. The process of claim 1, where the oxidizing substance is an aqueous solution of hydrogen peroxide in concentrations from 50 to 70% and in quantities of from 100 to 140% of the stoichiometric quantities with respect to the starting unsaturated fatty acid or ester.

5. The process of claim 1, wherein the catalyst from step (a) is present in quantity of from 0.1 to 1.1% by weight with respect to the starting unsaturated fatty acid or ester.

6. The process of claim 1, wherein it is conducted at a temperature from 50° C. to 90° C.

7. The process of claim 1, wherein the reaction time of step (a) is from 2 to 8 hours, and the reaction time for oxidation of the intermediate reaction product in step (b) is from 5 to 12 hours.

8. The process of claim 1, wherein the starting unsaturated fatty acid or ester is selected from the group consisting of oleic acid, erucic acid, palmitoleic acid, myristolic acid, 9-decalenic acid, 9-dodecalenic acid, ricinoleic acid, linoleic acid, linolenic acid, the corresponding esters of the foregoing acids with mono and polyvalent alcohols, and mixtures thereof.

* * * * *